United States Patent [19]

Iinuma et al.

[11] 4,416,286

[45] Nov. 22, 1983

[54] ULTRASONIC BLOOD FLOW MEASURING APPARATUS

[75] Inventors: Kazuhiro Iinuma, Yaita; Yasutsugu Seo, Otawara; Shigeru Sato, Chigasaki, all of Japan

[73] Assignee: Tokyo Shibaura Denki Kabushiki Kaisha, Kawasaki, Japan

[21] Appl. No.: 232,235

[22] Filed: Feb. 6, 1981

[30] Foreign Application Priority Data

Feb. 12, 1980 [JP] Japan .................................. 55-15811

[51] Int. Cl.³ .............................................. A61B 10/00
[52] U.S. Cl. ................................................. 128/663
[58] Field of Search ....................... 128/660, 661, 663; 73/861.25

[56] References Cited

U.S. PATENT DOCUMENTS

| | | | |
|---|---|---|---|
| 3,939,707 | 2/1976 | Kossoff | 73/194 A |
| 4,103,679 | 8/1978 | Aronson | 128/663 |
| 4,265,126 | 5/1981 | Papadofrongakis et al. | 128/663 X |
| 4,318,413 | 3/1982 | Iinuma et al. | 128/660 |

OTHER PUBLICATIONS

Borodzinski; K. et al., Quantitative Transcutaneous Measurements of Blood Flow in Carotid Artery by Means of Pulse and Continuous Wave Doppler Methods, Uts in Med. & Biol. vol. 2, #3, Jun. 1976, pp. 189-193.

Baker, D. W., "Pulsed Ultrasonic Doppler Blood-Flow Sensing," IEEE Transactions on Sonics and Ultrasonics, Jul. 1970, pp. 170-185.

*Primary Examiner*—Henry J. Recla
*Assistant Examiner*—Francis J. Jaworski
*Attorney, Agent, or Firm*—Finnegan, Henderson, Farabow, Garrett & Dunner

[57] ABSTRACT

An ultrasonic blood flow measuring apparatus comprising:
- an ultrasonic probe for transmitting an ultrasonic beam into a tissue under examination in response to an electrical driving pulse and for receiving an ultrasonic echo reflected from the tissue to convert the same into an electrical signal;
- a pulse generator arrangement for generating the electrical driving pulse of said probe;
- a detector circuit for detecting a tomogram signal from the electrical signal;
- a Doppler signal processing circuit for extracting Doppler frequency shift components due to velocity of a blood flow in the tissue from the electrical signal;
- a marker signal generator for generating marker signals indicative of a location where velocity of the blood flow is measured and a direction of the ultrasonic beam which contains the Doppler frequency shift components;
- an arithmetic circuit for calculating an angle $\theta$ defined between a direction of the blood flow and the direction of the ultrasonic beam which contains the Doppler frequency shift components;
- a divider circuit for obtaining the velocity of the blood flow in accordance with the Doppler frequency shift components and the angle $\theta$; and
- a display device for displaying a tomogram of the tissue and markers in response to the tomogram signal and the marker signals, respectively.

9 Claims, 5 Drawing Figures

ULTRASONIC BLOOD FLOW MEASURING APPARATUS

The present invention relates to an ultrasonic blood flow measuring apparatus of the type to which a blood flow measuring method by an ultrasonic Doppler effect and an ultrasonic tomography method are applied.

The conventional Doppler effect blood flow measuring apparatus has unfrequently been used since it can not specify a location of a tissue where a blood flow is measured. Recently, however, there has been developed a blood flow measuring apparatus employing the combination of the Doppler effect and the ultrasonic tomography methods, in which the measurement of velocity of the blood flow is conducted on the real time basis while observing a tomogram displayed on a screen. In the ultrasonic blood flow measuring apparatus a pulsed ultrasonic beam of a fixed frequency is radiated toward an object under examination and an ultrasonic echo is reflected therefrom. Since blood in the object circulates with a certain velocity, the echo reflected from blood-corpuscles, for example, includes Doppler frequency shift $f_d$ which is expressed by $$f_d = 2v/c \times f \quad (1)$$

where f is the fixed frequency of the pulsed ultrasonic beam, v is the velocity component of a blood flow in the direction of ultrasonic beam radiation, and c is the velocity of sound. Here, let V denote the velocity of a blood flow, and $\theta$ designate an angle defined by the blood flow direction and the ultrasonic beam direction, then $$v = V \cos \theta. \quad (2)$$

Thus equation (1) is rewritten into:

$$f_d = [(2V \cos \theta)/c] \times f \quad (3)$$

As seen from the equation (3), in order to obtain the blood flow velocity V from the Doppler frequency shift $f_d$, it is necessary to determine $\cos \theta$ (cosine value of the angle $\theta$).

A conventional method to determine $\cos \theta$ is such that the direction of the ultrasonic echo which containes Doppler frequency shift components is superposed on a tomogram, the tomogram is photographed, the angle $\theta$ on the photograph is measured by a protractor, and the cosine of the angle $\theta$ is obtained by using a trigonometric function table or through the calculation.

According to this method, the working of $\cos \theta$ is troublesome and time-consuming, being attendant with a measuring error due to the manual measuring of the angle.

Accordingly, an object of the present invention is to provide an ultrasonic blood flow measuring apparatus by which the working of the $\cos \theta$ is simple and quick with a high accuracy of the angle measurement by automatically calculating the $\cos \theta$ within the apparatus.

According to the present invention, there is provided an ultrasonic blood flow measuring apparatus comprising:

means for transmitting an ultrasonic beam into a tissue under examination in response to an electrical driving pulse and for receiving an ultrasonic echo reflected from the tissue to convert the same into an electrical signal;

means for generating the electrical driving pulse of said transmitting and receiving means;

means for detecting a tomogram signal from the electrical signal;

means for extracting Doppler frequency shift components due to velocity of a blood flow in the tissue from the electrical signal;

means for generating marker signals indicative of a location where velocity of the blood flow is measured and a direction of the ultrasonic beam which contains the Doppler frequency shift components;

means for calculating an angle $\theta$ defined between a direction of the blood flow and the direction of the ultrasonic beam which contains the Doppler frequency shift components;

means for obtaining the velocity of the blood flow in accordance with the Doppler frequency shift components and the angle $\theta$; and means for displaying a tomogram of the tissue and markers in response to the tomogram signal and the marker signals, respectively.

The present invention will be better understood when carefully reading the following description taken in connection with the accompanying drawings, in which:

FIG. 1 diagrammatically illustrates a basic method to measure velocity of a blood flow with the assistance of a tomogram by means of an ultrasonic blood flow measuring apparatus according to the present invention;

Figure 4:
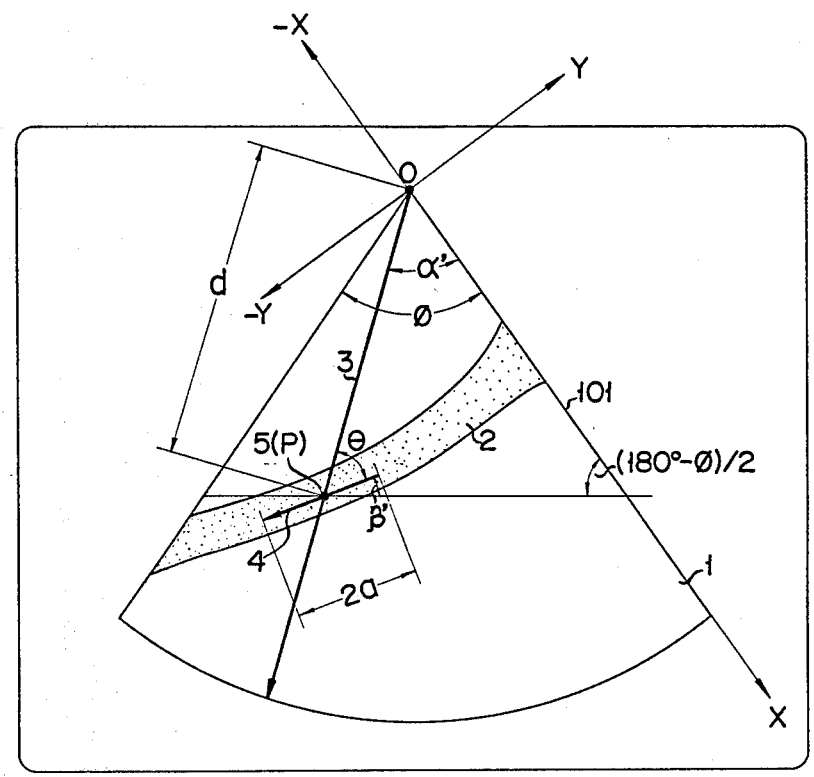
Figure 5:
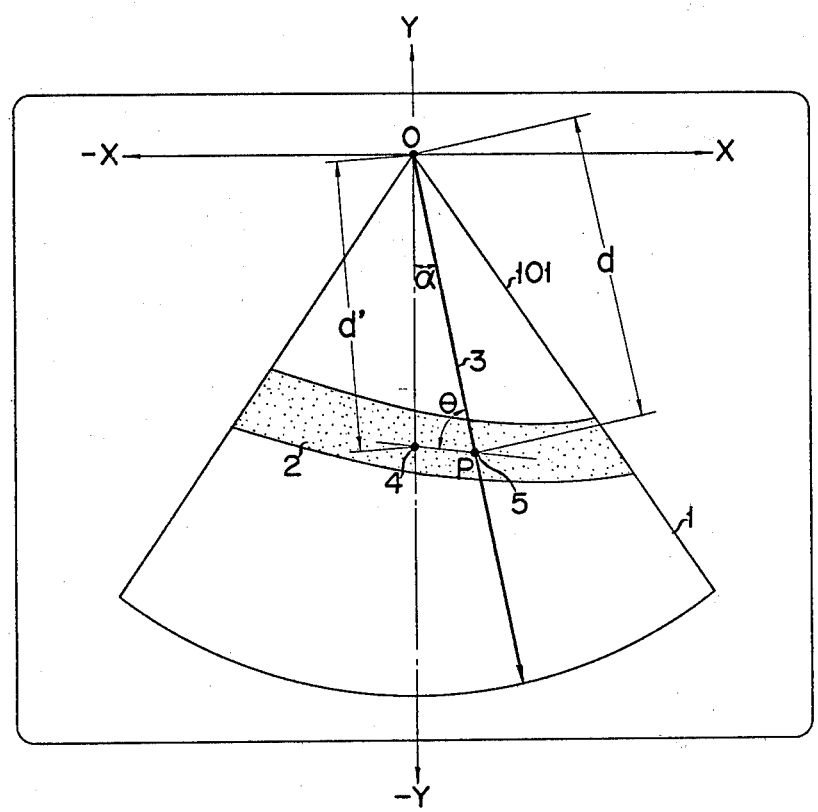

FIG. 4 diagrammatically illustrates another method to measure a blood flow in cooperation with a tomogram by means of the ultrasonic blood flow measuring apparatus according to the present invention; and FIG. 5 diagrammatically illustrates yet another method to measure a blood flow in combination with a tomogram by means of the ultrasonic blood flow measuring apparatus according to the present invention.

Figure 1:
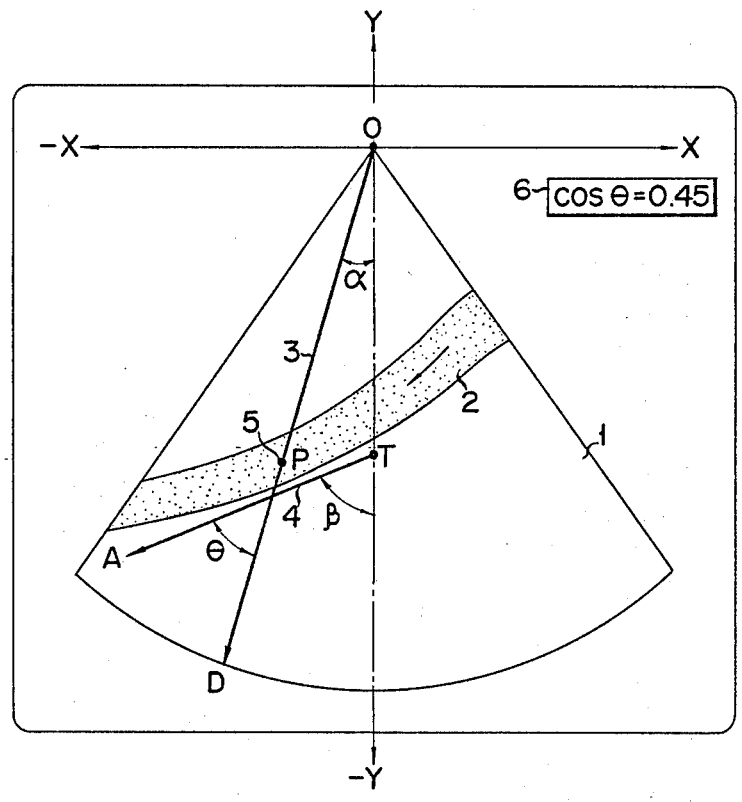

A principle method for measuring velocity of a blood flow which is applied to an ultrasonic blood flow measuring apparatus according to the present invention will be described referring to FIG. 1. FIG. 1 illustrates an example of a tomogram displayed on a CRT display device when velocity of the blood flow is measured by the ultrasonic blood flow measuring apparatus according to the present invention. In this example, a tomogram 1 is formed by a sector electronic scanning of ultrasonic beams and has a sector shape. A blood vessel 2 with a blood flow to be measured is tomographed on the screen.

For obtaining the velocity V of the blood flow at a point P in a blood vessel 2 by using the tomogram, the ultrasonic beam is radiated so as to pass through a line extending from a point O as a center of an ultrasonic probe through a point P. A straight line $\overline{OD}$ including points O and P is displayed on the tomogram, as a marker 3 for indicating a direction of the ultrasonic beam which contains the Doppler frequency shift components. A line $\overline{TA}$ extending from a point T on a center line is displayed on the tomogram as another marker 4 for indicating a direction of the blood flow to be measured. The center line is indicated by a one-dot chain line extending along a Y axis from the center point O. The marker 4 is adjusted, by an operator, so as to be substantially parallel to the direction of the blood flow, as shown, while observing the tomogram.

When the markers 3 and 4 are set in this way, the angle $\theta$ between the blood flow direction and the direction of the ultrasonic beam containing the Doppler frequency shift components is obtainable by the following equation, as seen from the drawing.

$$\theta = \beta - \alpha \quad (4)$$

where $\beta$ is an angle between the center line and the line segment $\overline{TA}$, or the marker 4, $\alpha$ is an angle between the center line and the line segment $\overline{OD}$, or the marker 3 for the ultrasonic beam direction. The angles $\beta$ and $\alpha$ can be obtained on the real time basis at the same time when setting of the markers 3 and 4 is completed as will be described later. Therefore, by using those angles $\beta$ and $\alpha$ the angle $\theta$ and its cosine (cos $\theta$) can be automatically calculated in the blood flow measuring apparatus according to this invention.

Figure 2:
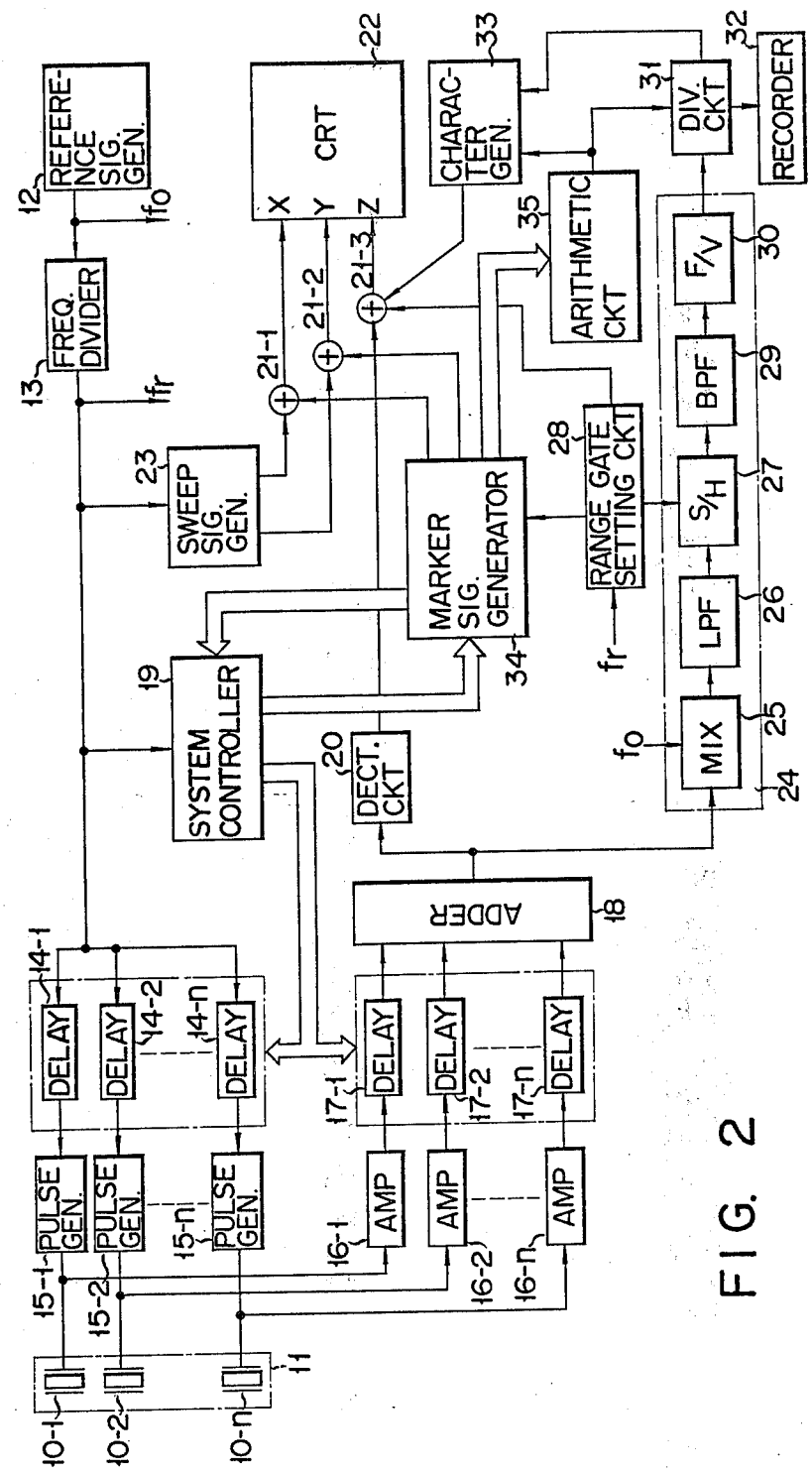
FIG. 2 is a block diagram of an embodiment of an ultrasonic blood flow measuring apparatus according to the present invention.

Turning now to FIG. 2, there is shown a block diagram of an ultrasonic blood flow measuring apparatus implementing the principle method.

In the figure, an ultrasonic probe 11 consists of phased array transducers 10-1 to 10-n. The transducers 10-1 to 10-n are respectively driven by pulse generators 15-1 to 15-n to radiate ultrasonic beams into a tissue in a sector scanning manner. The pulse generators 15-1 to 15-n are driven by rate pulses with delay times which are derived from a frequency divider 13 and passed through delay circuits 14-1 to 14-n. The frequency divider 13 divides clock pulses generated by a reference frequency signal generator 12. The ultrasonic beams is reflected from blood corpuscles in the blood flow of the tissue under examination to the transducers 10-1 to 10-n where those are converted into electrical signals. These electrical signals are applied through corresponding pre-amplifiers 16-1 to 16-n and delay circuits 17-1 to 17-n to an adder 18 where those are summed.

The delay times of the delay circuits 14-1 to 14-n are controlled by a system controller 19 so that the ultrasonic beams radiated from the transducers 10-1 to 10-n take a sector pattern. The same control is applied for the delay times of the delay circuits 17-1 to 17-n. As well known, the radiation directions of the ulrasonic beams radiated from and received by the probe 11 are steered by changing the delay times of the transducers, thereby to effect the sector scanning. The system controller 19 comprises, though not shown, a ROM (Read Only memory) for storing delay times of delay circuits 14 and 17 and control instructions of the apparatus, and a counter for counting output clock pulse of the frequency divider to generate an address of the ROM.

The output signal of the adder 18 is applied to a detector circuit 20 where it is subjected to the envelope detection. The detected signal is applied as an intensity modulation signal to a Z-terminal of a CRT (Cathode Ray Tube) display device 22 through an adder 21-3. A sweep signal generator circuit 23 generates X- and Y-sweep signals containing the information of the ultrasonic beam direction in response to instructions of the system controller and rate pulses of the frequency divider 13, which are applied to X- and Y-terminals of the CRT display device 22 through adders 21-1 to 21-2. As a result, the tomogram 1 with the sector pattern as shown in FIG. 1 is displayed on the screen of the display device 22.

The output signal from the adder 18 is also applied to a Doppler signal processing circuit 24. In the circuit 24, the output signal of the adder circuit 18 is firstly mixed, by a mixer circuit (MIX) 25, with a reference signal of a frequency $f_o$ from the reference signal generator 12, and then is passed through a low-pass filter (LPF) 26 where unnecessary harmonic components contained in the reflecting signal are removed. In this way, the echo signal is taken out as a phase-detected signal. The phase-detected signal is applied to a sample and hold (S/H) circuit 27 where it is sampled and held in accordance with an output of a range gate setting circuit 28. The output pulse is formed by delaying the rate pulse $f_r$ by $t_o = 2d/c$ (d indicates a depth from the center point O to the point P) in the range gate setting circuit 28. In this way, the Doppler information at the location with the depth d is obtained. The output signal of the sample/hold circuit 27 is filtered out by a band-pass filter (BPF) 29 to contain only the Doppler signal by the blood flow at the point P. The Doppler signal is applied to a frequency to voltage (F/V) converter 30 where it is converted into a voltage corresponding to the Doppler frequency shift $f_d$, which is taken out as an output signal from the Doppler signal processing circuit 24.

The output signal from the Doppler signal processing circuit 24 is transferred to a divider 31 where it is divided by a signal representing cos $\theta$ supplied from an arithmetic circuit 35 to be described later. The divider 31 produces a signal indicative of the blood flow velocity V through the division. The velocity signal is recorded by a recorder 32 or, as desired, is displayed on the screen of the CRT display device 22 after it is converted into a character signal by a character generator 33.

Figure 3:
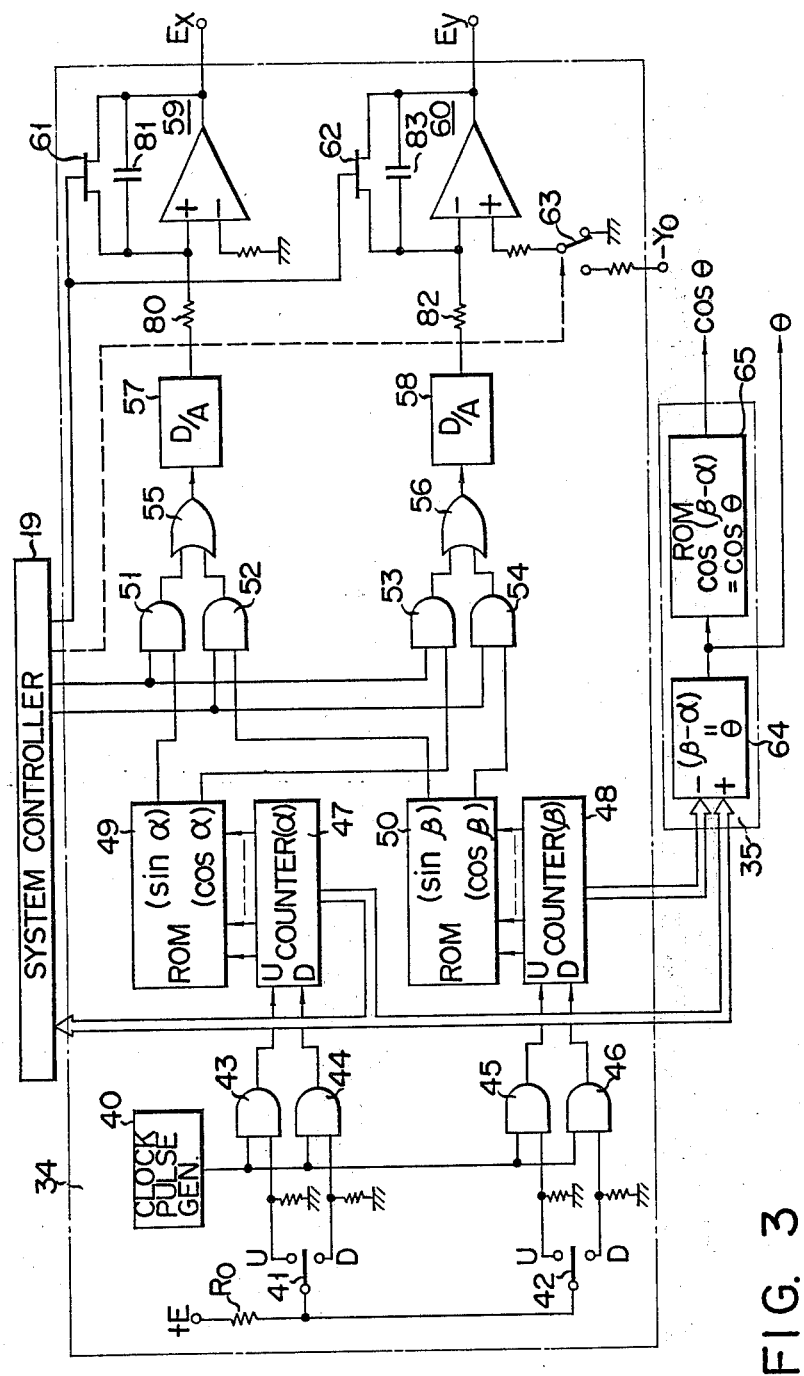
FIG. 3 is a block diagram of a marker signal generating circuit and an arithmetic circuit used in the ultrasonic blood flow measuring apparatus shown in FIG. 2.

FIG. 3 illustrates circuit arrangements for the marker signal generating circuit 34 and the arithmetic circuit 35 in detail.

The marker signal generating circuit 34 generates signals of the marker 3 for the ultrasonic beam direction and the marker 4 for the reference direction, which are displayed superposed on the tomogram 1 shown in FIG. 1. The arithmetic circuit 35 computes the angle $\theta$ between the markers 3 and 4 and the cos $\theta$. Switches 41 and 42 are used to set the angles $\alpha$ and $\beta$ by an operator. The movable contacts of the switches 41 and 42 are connected to a proper potential +E through a resistor Ro. When the switches 41 and 42, respectively, are turned to stationary contacts U, AND gates 43 and 45, respectively, are enabled, so that a clock pulse of a clock pulse generator 40 is supplied to the count-up terminals of reversible counters 47 and 48 through the gates 43 and 45. When the counters 47 and 48 are supplied with clock pulses of the generator 40 at the count-up terminals, the counters 47 and 48 start counting up, and their contents increase. On the other hand, when the switches 41 and 42, respectively, are turned to stationary contacts D, AND gates 44 and 46, respectively, are enabled, so that the clock pulse of the generator 40 is applied to the down-count terminals of the counters 47 and 48 through the AND gates 44 and 46. When the counters 47 and 48 are supplied with clock pulses of the generator 40 at the count-down terminals, the counters 47 and 48 start counting down, and their contents decrease. The contents of the counters 47 and 48 represent the angles $\alpha$ and $\beta$, respectively. The markers 3 and 4 are displayed on the display screen at the angles defined by the contents of the counters in a manner as described later. For setting the angle α, the switch 41 is manually operated by an operator while observing the CRT screen so that the marker 3 passes through the point P in the blood flow in FIG. 1. For setting the angle β, the switch 42 is operated in the same manner so that the marker 4 is substantially parallel to the blood flow direction. Since the contents of the counters 47 and 48 after such switch operations are digital data indicative of the angles α and β, respectively, the data processing is carried out easily and accurately.

The output signal of the counter 47 is applied as an address signal to a read only memory (ROM) 49 to read out data therefrom. The ROM 49 is stored with digital data of a sin α and cos α and provides the data to AND gates 51 and 53, respectively, in response to the address signal. Similarly the output signal of the counter 48 is applied as the address signal to a ROM 50 to read out data therefrom. The ROM 50, however, is stored with digital data of sin β and cos β and provides the data to AND gates 52 and 54, respectively, in response to the address signal.

The contents of the ROMs 49 and 50 are alternately read out in time-shared manner during a blanking period of the tomogram display. Specifically, at a time in the blanking period of the tomogram, the system controller 19 enables the AND gates 51 and 53 so that data of the sine α are transferred through the AND gate 51 and an OR gate 55 to a D/A (digital to analog) converter 57, which, in turn, converts the data into an analog signal. The analog signal is applied through a resistor 80 to the non-inverting terminal of an integration circuit 59. Data of the cos α from the ROM 49 are also applied through the AND gate 53 and an OR gate 56 to a D/A converter 58 which converts the data into an analog signal. The analog signal is then applied through a resistor 82 to the inverting terminal of an integration circuit 60.

Therefore, the operation polarities of the integration circuits 59 and 60 are opposite to each other. The reason for this is that the scanning beam line of the tomogram to be displayed on the CRT screen is radiated in the negative direction of the Y axis. Simultaneously with the radiation of the ultrasonic pulse, the integration circuits 59 and 60 start the integrating operation by turning on MOS transistor switches 61 and 62 at the time enabling signals of controller 19 are applied to control gates thereof, respectively. While a switch 63 connected to the non-inverting input terminal of the integration circuit 60 has been already turned to ground under control of the system controller 19. The output signals $E_X$ and $E_Y$ from the integration circuits 59 and 60 are expressed with respect to time t by equations (5).

$$E_X = \frac{t}{R1 \cdot C1} \sin \alpha \\ E_Y = -\frac{t}{R2 \cdot C2} \cos \alpha \quad \bigg\} \quad (5)$$

where R1 and C1, respectively, are values of resistance of an integrating resistor 80 and capacitance of a capacitor 81 in the integrator 59, and R2 and C2, respectively, are those of resistance of an integrating resistor 82 and capacitor of an integrating capacitor 83 in the integrator 60.

The output signals $E_X$ and $E_Y$ of the integrators 59 and 60, respectively, are applied as the marker signals to the X- and Y-terminals of the CRT display device 22 through the adders 21-1 and 21-2 (see FIG. 1). In this way, the marker 3 for indicating the Doppler ultrasonic beam direction on the tomogram in FIG. 1 is displayed on the CRT screen 22.

At another time in the blanking period of the tomogram, under control of the system controller 19, AND gates 52 and 54 are enabled so that data of the sine β from the ROM 50 are applied through the AND gate 52 and the OR gate 55 to the D/A converter 57. The output signal of the converter 57 is applied through the resistor 80 to the non-inverting terminal of the integrator 59. Data of the cos β are applied through the AND gate 54 and the OR gate 56 to the D/A converter 58. The output signal of the converter 58 is then applied to the inverting terminal of the integrator 60. At this time, the switch 63 has been turned to a negative fixed voltage -Yo under control of the system controller 19. In this case, the output signals $E_X$ and $E_Y$ of the integrators 59 and 60 are expressed as follows $$E_X = \frac{t}{R1 \cdot C1} \sin \beta \\ E_Y = -Y_o + \frac{t}{R2 \cdot C2} \cos \beta \quad \bigg\} \quad (6)$$

These output signals $E_X$ and $E_Y$ are applied to the X- and Y-terminals of the CRT display device 22. In this way, the marker 4 for indicating the reference direction on the tomogram is displayed on the CRT display device 22.

The markers 3 and 4 are rotated on the screen about the points O and T by operating the switches 41 and 42, respectively, since the contents of the counters 47 and 48 associated with the switches 41 and 42 are changed by the switch operations. Therefore, when the switch 41 is operated so that the marker 3 passes through the point P, the contents of the counter 47 indicates the angle α. Similarly, when the switch 42 is operated so that the marker 4 is substantially parallel to the blood flow direction, the contents of the counter 48 indicates the angle β.

In this way, the angle data α and β about the direction of the ultrasonic beam and the reference direction may be obtained from the counters 47 and 48, respectively, on the real time basis at the same time when setting of the markers 3 and 4 is completed. Thus, obtaining the angle α, all the operator has to do is to merely operate the switch 41, while observing the display screen, so that the marker 3 passes through the point P in the blood vessel. For obtaining the angle β, the operation to be made by the operator is to merely adjust the marker 4 so that it is tangential to the blood flow by means of the switch 42. Accordingly, the angle θ between the blood flow direction and the reference direction may be obtained by using the output signals from the counters 47 and 48.

In the present embodiment, for calculating the angle θ, the outputs of the counters 47 and 48 are supplied to the arithmetic circuit 35 (where (β−α) is performed by a subtractor 64 in the arithmetic circuit 35 as shown in FIG. 3. Since the signal of the angle θ is supplied as an address information to a ROM (Read Only Memory) 65, data of cos θ stored therein are read out. In this way, the cos θ is obtained in the ultrasonic blood flow measuring apparatus of the present invention.

The cos θ data thus obtained is applied through a D/A converter (not shown), if desired, to the divider 31 as previously mentioned. Numerical data of cos θ may also be displayed together with the tomogram 1 on the screen of the CRT display device 22 after applied thereto through the character generator 33. The displayed character data of cos θ may be photographed for a later use. Alternatively, the angle θ or the blood flow velocity V may be displayed in place of the cos θ.

Data on the angle α from the counter 47 are applied to the system controller 19. Upon receipt of the data, the system controller 19 controls the delay times of the delay circuits 14-1 to 14-n and the delay circuits 17-1 to 17-n so that the ultrasonic beam has a deflection angle of α at a fixed time interval, for example, every other period of the rate pulse and steers the same so as to make the sector scanning during the remaining period.

In FIG. 2, the range gate pulse of the range gate setting circuit 28 is also applied to the Z-terminal of the CRT display device 22 through the adder 21-3. With the range gate pulse, a marker 5 for indicating the blood flow measuring location is displayed at the point P on the CRT display device 22, as shown in FIG. 1.

FIGS. 4 and 5 diagrammatically illustrate other ways of measuring the blood flow with the assistance of the tomogram by using the ultrasonic blood flow measuring apparatus according to the invention. The measuring way of FIG. 4 locates the marker 3 for the reference direction representing the blood flow direction on the point P, or the marker 5.

It is assumed that the point O is located at the tissue $(x_o, y_o) = (O, O)$ in the X-Y co-ordinates system, and that the scanning line 101 lies on the X-axis. On this assumption, the point P lies at the following coordinates $$(x_p, y_p) = (d \cos \alpha', -d \sin \alpha') \qquad (7)$$

The location of the marker 4 for the reference direction is $$(x, y) = (r \cos \beta' + X_p, r \sin \beta' + Y_p) \qquad (8)$$

where r is expressed by $-a < r < a$ ($2a$ is the length of the marker 4). Here, the angle θ between the blood flow direction and the direction of the Doppler ultrasonic beam is given by $$\theta = 180° - \alpha' - \frac{180° - \phi}{2} - \beta' \qquad (9)$$

$$= 90° - \alpha' - \beta' + \phi/2$$

where $\phi$ is a display angle (sector angle) of the tomogram 1, $\alpha'$ is an angle between the scanning line 101 and the marker 3, and $\beta'$ is an angle between a straight line crossing the scanning line 101 at an angle $(180° - \phi)/2$ and passing the point P and the marker 4. Accordingly, if in the marker signal generating circuit 34, the angles $\alpha'$ and $\beta'$ are set to form a marker signal, the angle θ in the equation (9) and the cos θ may be calculated in the arithmetic circuit 35 by using the angles $\alpha'$ and $\beta'$, further the cos θ may be calculated. It is evident that the display as shown in FIG. 4 is possible by using the angles α and β in place of the $\alpha'$ and $\beta'$.

In the example of FIG. 5, the reference direction marker 4 is displayed as a dot, which was bar-shaped in the examples in FIGS. 1 and 4. In this case, if the marker 4 is displayed lying on the center line parallel to the Y-axis, the cos θ is $$\cos \theta = (d - d' \cos \alpha) / \sqrt{d^2 + d'^2 - 2dd' \cos \alpha} \qquad (10)$$

In this example, the additional factor d' (distance from the point O to the marker 4) is needed; however, it may be obtained in the stage of forming the marker signal for the marker 4. Accordingly, by solving the equation (10) by using it, the cos θ may be obtained.

As described above, according to the present invention, the angle θ and cos θ may automatically be obtained in the apparatus by operating the switch 41 so that the marker 3 lies on the point P and by operating the switch 42 so that the marker 4 is substantially parallel to the blood flow direction, as shown in FIG. 1. The switch operations are made while observing the tomogram on the CRT screen. Therefore, the blood flow measuring work may be made simply and rapidly and the accuracy of the measurement is increased.

Particularly, the angle θ and the cos θ may be obtained on real time basis so that the measurement is free from time variation of the angle θ and of the Doppler shift (which correspondingly changes if the former changes).

The present invention is not limited to the above-mentioned embodiment but may be changed and modified variously. For example, the scanning method for obtaining the tomogram may be the linear scanning or the mechanical scanning in place of the sector scanning employed in the above-mentioned embodiment. The probes may be individually provided for the transmission and reception of the ultrasonic beams, although the above-mentioned embodiment employs a single sector scanning probe for both the purposes. In this case, the drive control systems for the probes and the signal processing systems may also be provided separately for the respective probes.

If the reference direction of the blood flow is set so as to be parallel to the blood flow direction in the blood vessels except those of a heart, the processing for the measurement is simple and effective. In the blood flow measurement in the heart, it is difficult to select the direction of the blood flow. In this case, one of the preferable ways is to select the reference direction of the blood flow in the longitudinal direction of the heart.

What we claim is:

1. An ultrasonic blood flow measuring apparatus comprising:

transducer means for transmitting an ultrasonic beam into an object, receiving an ultrasonic echo reflected from the object, and converting such echo into an electrical signal;

scanning means for scanning the object with said ultrasonic beam;

first detecting means for detecting a tomogram signal of the object from said electrical signal;

display means for displaying said tomogram of the object corresponding to said tomogram signal;

second detecting means for extracting a Doppler signal from said electrical signal;

marker generating means responsive to operator control for selectively locating on said display means and superimposed over said tomogram both a first marker indicative of a selected first direction in which said ultrasonic beam travels when passing through a selected portion of a vessel in the object in which the blood flow is to be measured, and a second marker which is indicative of a second direction in which blood flows through said portion of said vessel; and calculating means responsive to the location of said first and second markers on said display means for calculating an angle $\theta$ defined by said first and second directions and for calculating the velocity of the blood flow through said portion of said vessel based on said Doppler signal and said angle $\theta$.

2. An ultrasonic blood flow measuring apparatus according to claim 1 wherein said calculating means includes means for generating $\alpha$ which is an angle between a reference axis set on the tomogram and said first direction, means for generating $\beta$ which is an angle between the reference axis and said second direction, and means for generating said angle $\theta$ by subtracting $\alpha$ from $\beta$.

3. An ultrasonic blood flow measuring apparatus according to claim 2 wherein said marker generating means comprises first memory means for storing digital data indicative of sin $\alpha$ and cos $\alpha$, $\alpha$ being an angle between a reference axis set on the tomogram and said first direction; first operating means for determining said first direction to set the angle $\alpha$; first counter means for counting clock pulses corresponding to the angle $\alpha$ in accordance with an amount of operation of said first operating means and for delivering digital data indicative of the angle $\alpha$ to said first memory means so that the first memory means may generate digital data indicative of sin $\alpha$ and cos $\alpha$; first generating means for integrating the digital data of sin $\alpha$ and cos $\alpha$ from said first memory means; second memory means for storing digital data indicative of sin $\beta$ and cos $\beta$, $\beta$ being an angle between the reference axis and said second direction; second operating means for determining said second direction to set the angle $\beta$; second counter means for counting clock pulses corresponding to the angle $\beta$ in accordance with the amount of operation of said second operating means and for delivering digital data indicative of the angle $\beta$ to said second memory means so that the second memory means may generate digital data indicative of sin $\beta$ and cos $\beta$; and second integrating means for integrating the digital data of sin $\beta$ and cos $\beta$ from said second memory means.

4. An ultrasonic blood flow measuring apparatus according to claim 2, wherein said marker generating means comprises a clock pulse generating means, first and second operating means for determining said first and second directions, respectively, a first counter for counting output clock pulses of said clock pulse generator under control of said first operating means, a second counter for counting output clock pulses of said clock pulse generating means under control of said second operating means, first memory means which receives the contents of said first counter as address information and converts the same to sine and cosine data, second memory means which receives the contents of said second counter as address information and converts the same to sine and cosine data, a first digital-to-analog converter for converting the output data of said first memory means into analog data, a second digital-to-analog converter for converting the output data from said second memory means into analog data, first and second integrating means for integrating the output signals from said first and second digital-to-analog converters, respectively.

5. An ultrasonic blood flow measuring apparatus according to claim 4, wherein said calculating means comprises subtracting means for obtaining a difference between the contents of said first and second counters and data converting means which receives the difference data of said subtracting means as addressing information and converts the same to cosine data.

6. An ultrasonic blood flow measuring apparatus according to claim 5, wherein said data converting means comprises a ROM which is stored with cosine data and which receives the difference data of said subtracting means as an addressing information to convert the same cosine data.

7. An ultrasonic blood flow measuring apparatus according to claim 4, wherein said first operating means comprises a first switching means having a movable terminal and first and second stationary terminals, the movable terminal being connected to a predetermined voltage potential, a first gate means of which first and second input terminals are connected to the first stationary terminal of said first switching means and said clock pulse generating means, respectively, said first gate means opening when said movable contact of the first switching means being in contact with said first stationary terminal thereof, thereby transferring clock pulses of said clock pulse generating means to an up-counting terminal of said first counter, and a second gate means of which first and second input terminals are connected to the second stationary terminal of said first switching means and said clock pulse generating means, respectively, said second gate means opening when said movable contact of the first switching means being in contact with said second stationary terminal thereof, thereby transferring clock pulses of said clock pulse generating means to an down-counting terminal of said first counter, and said second operating means comprises a second switching means having a movable terminal and first and second stationary terminals, the movable terminal being connected to the predetermined voltage potential, a third gate means of which first and second input terminals are connected to the first stationary terminal of said second switching means and said clock pulse generating means, respectively, said third gate means opening when said movable contact of the second switching means being in contact with said first stationary terminal thereof, thereby transferring clock pulses of said clock pulse generating means to an up-counting terminal of said second counter, and a fourth gate means of which first and second input terminals are connected to the stationary terminal of said second switching means and said clock pulse generating means, respectively, said fourth gate means opening when said movable contact of the second switching means being in contact with said second stationary terminal thereof, thereby transferring clock pulses of said clock pulse generating means to an down-counting terminal of said second counter.

8. An ultrasonic blood flow measuring apparatus according to claim 4, wherein said first memory means comprises a ROM which is stored with sine data and cosine data and which receives the contents of said first counter as an addressing information to convert the same sine data and cosine data.

9. An ultrasonic blood flow measuring apparatus according to claim 4, wherein said second memory means comprises a ROM which is stored with sine data and cosine data and which receives the contents of said second counter as an addressing information to convert the same sine data and cosine data.

* * * * *